US010108778B2

(12) United States Patent
Colwell et al.

(10) Patent No.: US 10,108,778 B2
(45) Date of Patent: Oct. 23, 2018

(54) METHOD AND SYSTEM FOR GENOME IDENTIFICATION

(71) Applicant: COSMOSID, INC., College Park, MD (US)

(72) Inventors: Rita R. Colwell, Bethesda, MD (US); John P. Jakupciak, Boonsboro, MD (US); Jongsik Chun, Rockville, MD (US)

(73) Assignee: CosmosID Inc., Rockville, MD (US)

( * ) Notice: Subject to any disclaimer, the term of this patent is extended or adjusted under 35 U.S.C. 154(b) by 475 days.

(21) Appl. No.: 14/291,930

(22) Filed: May 30, 2014

(65) Prior Publication Data

US 2014/0343868 A1 Nov. 20, 2014

Related U.S. Application Data

(63) Continuation of application No. 12/276,037, filed on Nov. 21, 2008, now Pat. No. 8,775,092.

(60) Provisional application No. 60/989,641, filed on Nov. 21, 2007.

(51) Int. Cl.
| G06F 19/22 | (2011.01) |
| G06F 19/10 | (2011.01) |
| G06F 19/00 | (2018.01) |
| G06F 19/28 | (2011.01) |

(52) U.S. Cl.
CPC ............ *G06F 19/22* (2013.01); *G06F 19/28* (2013.01)

(58) Field of Classification Search
None
See application file for complete search history.

(56) References Cited

U.S. PATENT DOCUMENTS

| 4,923,978 | A | 5/1990 | McCormick |
| 5,057,426 | A | 10/1991 | Henco et al. |
| 5,218,099 | A | 6/1993 | Reyes et al. |
| 5,733,729 | A | 3/1998 | Lipshutz et al. |
| 5,871,697 | A | 2/1999 | Rothberg et al. |
| 5,982,932 | A | 11/1999 | Prokoski |
| 7,602,785 | B2 | 10/2009 | Dharmapurikar et al. |
| 7,680,790 | B2 | 3/2010 | Indeck et al. |
| 7,702,683 | B1 | 4/2010 | Kirshenbaum |
| 7,870,385 | B2 | 1/2011 | Risan et al. |
| 2002/0120408 | A1 | 8/2002 | Kreiswirth et al. |
| 2003/0044771 | A1 | 3/2003 | Anderson et al. |
| 2003/0233197 | A1 | 12/2003 | Padilla et al. |
| 2004/0219580 | A1 | 11/2004 | Dunn et al. |
| 2005/0086520 | A1 | 4/2005 | Dharmapurikar et al. |
| 2005/0120408 | A9 | 6/2005 | Reuber et al. |
| 2005/0149272 | A1 | 7/2005 | Pe'Er et al. |
| 2005/0255459 | A1 | 11/2005 | Fofanov et al. |
| 2006/0259249 | A1 | 11/2006 | Sampath et al. |
| 2007/0067108 | A1 | 3/2007 | Buhler et al. |
| 2007/0260602 | A1 | 11/2007 | Taylor |
| 2007/0263163 | A1 | 11/2007 | Mun et al. |
| 2009/0158008 | A1 | 1/2009 | Colwell et al. |
| 2009/0150084 | A1 | 6/2009 | Colwell et al. |
| 2009/0270277 | A1 | 10/2009 | Glick et al. |
| 2009/0319506 | A1 | 12/2009 | Ngan |
| 2010/0049445 | A1 | 2/2010 | Fofanov et al. |

FOREIGN PATENT DOCUMENTS

| EP | 0515484 B1 | 4/1995 |
| EP | 0512767 A1 | 7/1996 |
| WO | WO 95/13368 | 5/1995 |
| WO | WO 96/18731 | 6/1996 |
| WO | WO 97/10331 | 3/1997 |
| WO | WO 2004/007763 | 1/2004 |
| WO | WO 2006/096324 | 9/2006 |

OTHER PUBLICATIONS

Buhler et al., "Mercury BLASTN: Faster DNA Sequence Comparison Using a Streaming Hardware Architecture," Proc. of Reconfigurable Systems Summer Institute, Jul. 2007 (11 pages).
Kent, "BLAT—The BLAST-Like Alignment Tool," Genome Res., vol. 12, pp. 656-664 (2002).
Ning et al., SSAHA: Fast Search Method for Large DNA Databases, Genome Res., vol. 11, pp. 1725-1729 (2001).
Rosen et al., "Signal Processing for Metagenomics: Extracting Information from the Soup," Current Genomics, vol. 10, pp. 493-510 (2009).
Rumble et al., :SHRiMP: Accurate Mapping of Short Color-space Reads, PLos Comput Biol, vol. 5, issue 5, e1000386, 11 pages (2009).
Stranneheim et al., "Classification of DNA Sequences Using Bloom Filters," Bioinformatics, vol. 26, No. 13, pp. 1595-1600 (2010).

(Continued)

*Primary Examiner* — Lori A. Clow
(74) *Attorney, Agent, or Firm* — Sheppard Mullin Richter & Hampton LLP

(57) ABSTRACT

The present invention belongs to the field of genomics and nucleic acid sequencing. It involves a novel method of sequencing biological material and real-time probabilistic matching of short strings of sequencing information to identify all species present in said biological material. It is related to real-time probabilistic matching of sequence information, and more particular to comparing short strings of a plurality of sequences of single molecule nucleic acids, whether amplified or unamplied, whether chemically synthesized or physically interrogated, as fast as the sequence information is generated and in parallel with continuous sequence information generation or collection.

14 Claims, 10 Drawing Sheets

(56) References Cited

OTHER PUBLICATIONS

Zhu et al., "Bayesian Adaptive Sequence Alignment Algorithms," Bioinformatics, vol. 14, No. 1, pp. 25-39 (1998).
J. P. Jakupciak, et al., "Barcoding Methodology and Applications—Biological agent detection technologies," Molecular Ecology Resources, vol. 9, Suppl. 1, pp, 51-57 (May 2009).
Rannala et al. (Journal of Mol. Evol. (1996) vol. 43, pp. 304-311).
Sagot et al. (Theoretical Computer Science (1997) vol. 180, pp. 115-137).
Ludwig et al. (Nucleic Acids Research (2004) vol. 32, pp. 1363-1371).
Huson et al. Genome Research (2007) vol. 17, pp. 377-386; first published online on Jan. 25, 2007.
Pavesi et al. (Bioinformatics (2001) vol. 17, Suppl. 1, pp. S207-S214).
Cowan et al. (Trends in Biotechnology (2005) vol. 23, No. 6, pp. 321-329).
Tringe et al. (Science (2005) vol. 308, pp. 554-557).
Ivnitski et al. (Biotechniques (2003) vol. 35, pp. 862-869).
European Office Action dated May 19, 2015 for Appln. No. 08 867 952.7-1405.
U.S. Office Action dated Aug. 31, 2016 for U.S. Appl. No. 13/934,029.
U.S. Office Action dated Mar. 31, 2016 for U.S. Appl. No. 13/934,029.
Extended European Search Report dated Mar. 8, 2016 for Appln. No. 12739779.2.
U.S. Office Action dated Oct. 27, 2015 for U.S. Appl. No. 13/934,029.
Indian Office Action dated Dec. 15, 2016 for Appln. No. 221/KOLNP/2010.
Zhu et al., "Bayesian adaptive sequence alignment algorithms", Bioinformatics, vol. 14, No. 1, 1998, pp. 25-39.
Final Office Action U.S. Appl. No. 13/934,029 dated May 23, 2017.

METHOD AND SYSTEM FOR GENOME IDENTIFICATION

CROSS REFERENCES TO RELATED APPLICATION

This application is a continuation of U.S. patent application Ser. No. 12/276,037, filed Nov. 21, 2008, which in turns claims priority to U.S. Provisional Patent Application No. 60/989,641, filed Nov. 21, 2007, the entire content of all applications are incorporated herein by reference in their entireties.

FIELD OF THE INVENTION

This invention relates to a system and methods for the identification of organisms and more particularly, to the determination of sequence of nucleic acids and other polymeric or chain type molecules by probabilistic data matching in a handheld or larger electronic device.

BACKGROUND

There are a wide variety of life-threatening circumstances in which it would be useful to analyze, and sequence a DNA or RNA sample, for example, in response to an act of bioterrorism where a fatal pathogenic agent had been released into the environment. In the past, such results have required involvement of many people, which demand too much time. As a result, rapidity and accuracy may suffer.

In the event of a bioterrorist attack or of an emerging epidemic, it is important that first responders, i.e. physicians in the emergency room (their options or bed-side treatments), as well as for food manufacturers, distributors, retailers, and for public health personnel country wide to rapidly, accurately, and reliably identify the pathogenic agents and the diseases they cause. Pathogenic agents can be contained in sample sources such as food, air, soil, water, tissue and clinical presentation of pathogenic agents. Because the agents and/or potential diseases may be life-threatening and be highly contagious, this identification process should be done quickly. This is a significant weakness in current homeland security bioterrorism response.

A system and method are needed which can identify more than a single organism (multiplexing) and indicate if a species is present, based on the genome comparison of nucleic acids present in a sample.

Rapid advances in biological engineering have dramatically impacted the design and capabilities of DNA sequencing tools, i.e. high throughput sequencing, which is a method of determining the order of bases in DNA, yielding a map of genetic variation which can give clues to the genetic underpinning of human disease. This method is very useful for sequencing many different templates of DNA with any number of primers. Despite these important advances in biological engineering, little progress has been made in building devices to quickly identify the sequence [information] and transfer data more efficiently and effectively.

Traditionally DNA sequencing was accomplished by a dideoxy method, commonly referred to as the Sanger method [Sanger et al, 1977], that used chain terminating inhibitors to stop the extension of the DNA chain by DNA synthesis.

Novel methods for sequencing strategies continue to be developed. For example the advent of DNA microarrays makes it possible to build an array of sequences and hybridize complementary sequences in a process commonly referred to as Sequencing-by-hybridization. Another technique considered current state-of-the-art employs primer extension followed by cyclic addition of a single nucleotide with each cycle followed by detection of the incorporation event. The technique, commonly referred to as Sequencing-by-synthesis or pyrosequencing, including fluorescent in situ sequencing (FISSEQ), is reiterative in practice and involves a serial process of repeated cycles of primer extension while the target nucleotide sequence is sequenced.

Thus, a need exists for rapid genome identification methods and systems, including multidirectional electronic communications of nucleic acid sequence data, clinical data, therapeutic intervention, and tailored delivery of therapeutics to the proper population to streamline responses, conserve valuable medical supplies, and contain bioterrorism, inadvertent release, and emerging pathogenic epidemics.

The current system is designed to analyze any sample that contains biological material to determine the presence of species or genomes in the sample. This is achieved by obtaining the sequence information of the biological material and comparing the sequencing information against a data base(s). Sequence information that match will indicate the presence of a genome or species. Probabilistic matching will calculate the likelihood that species are present. The methods can be applied on massively parallel sequencing systems.

SUMMARY OF INVENTION

One aspect of the present invention is a method of identifying a biological material in a sample, comprising: obtaining a sample comprising said biological material, extracting one or more nucleic acid molecule(s) from said sample, generating sequence information from said nucleic acid molecule(s) and probabilistic-based comparing said sequence information to nucleic acid sequences in a database. Identifying a biological material includes, but not limited to, detecting and/or determining the genomes present in the sample, nucleic acid sequence information contained within, said sample, ability determining the species of the a biological material, ability to detect variations between strains, mutants and engineered organisms and characterizing unknown organisms and polymorphisms. Biological material includes, but not limited to, DNA, RNA and relevant genetic information of organisms or pathogens.

In one embodiment of the invention, said one or more nucleic acid molecule(s) can be selected from DNA or RNA.

In another embodiment, the invention comprises generating the sequence information comprising a nucleotide fragment of "n" length, and further comparing said "n" length fragment to the nucleic acid sequences in a database.

In one embodiment, "n" represents a minimal length of the nucleotide fragment that is required for a positive identification of the nucleic acid molecule(s) obtained from said sample.

In one embodiment "n" can range from one nucleotide to five nucleotides.

In another embodiment of the invention, if the probability of match of the sequence information of "n" length nucleotide fragment is less than a threshold of a target match, then a nucleotide fragment of "n+1", "n+2" . . . "n+x" in length is generated.

In yet another embodiment, the invention comprises amplification of said one or more nucleic acid molecule(s) to yield a plurality "i" of one or more nucleic acid molecules, prior to generating sequence information. The sequence information generated after amplification may comprise nucleotide fragments of "n" length, such that a plurality "i(n)" number of fragments are compared to the nucleic acid sequences in a database.

In another embodiment of the invention, if the probability of match of the plurality "i(n)" of sequence information is less than a threshold of a target match, then a plurality of "i(n+1)", "i(n+2)" . . . "i(n+x)" sequence information is generated.

In one embodiment of the invention, the nucleotide fragment is compared to the nucleic acid sequences in a database via probabilistic matching, including, but not limited to Bayesian approach, Recursive Bayesian approach or Naïve Bayesian approach.

Probabilistic approaches may use Bayesian likelihoods to consider two important factors to reach an accurate conclusion: (i) $P(t_i/R)$ is the probability that an organism exhibiting test pattern R belongs to taxon $t_i$, and (ii) $P(R/t_i)$ is the probability that members of taxon $t_i$ will exhibit test pattern R. The minimal pattern within a sliding window integrated into the tools will assist investigators on "whether" and "how" organisms have been genetically modified.

In one embodiment of the invention, the probabilistic matching provides a hierarchical statistical framework to identify the species of said sequence information.

In another embodiment of the invention the comparison of the sequence information is performed, in real-time, or as fast as, or immediately after said sequence information is generated.

In another embodiment of the invention, the comparison of said sequence information is performed, in real-time, or as fast as the sequence information is generated, while additional sequence information continues to be generated from said one or more nucleic acid molecule(s), wherein said additional sequence information may comprise nucleotides of varying lengths, including, but not limited to, increased, decreased or same length of sequence information as compared to previously generated sequence information.

In another embodiment of the invention, the method comprises obtaining a sample comprising said biological material, extracting one or more nucleic acid molecule(s) from said sample, generating sequence information from said nucleic acid molecule(s), wherein said sequence information comprises a nucleotide fragment of "n" length, and comparing, in real-time, or as fast as the fragment is generated to the nucleic acid sequences in a database; while nucleic acid fragments of "n+1", "n+2" . . . "n+x" length continue to be generated from said one or more nucleic acid molecule(s) and compared, in real-time, or as fast as the fragments are generated, to the nucleic acid sequences in a database.

In another embodiment of the invention, the method comprises obtaining a sample comprising said biological material, extracting one or more nucleic acid molecule(s) from said sample, amplifying, said one or more nucleic acid molecule(s) to yield a plurality "i" of nucleic acid molecules before generating sequence information of "n" length nucleotide fragments; further comprising comparing the plurality "i(n)" of nucleotide fragments, in real-time, or as fast as the fragments are generated, to the nucleic acid sequences in a database; while a plurality "i(n+1)", "i(n+2)" . . . "i(n+x)" of nucleic acid fragments continue to be generated from said one or more nucleic acid molecule(s) and compared, in real-time, or as fast as the fragments are generated, to the nucleic acid sequences in a database.

In one embodiment of the invention, sequence information includes, but not limited to, a chromatogram, image of labeled DNA or RNA fragments, physical interrogation of a nucleic acid molecule to determine the nucleotide order, nanopore analyses, and other methods known in the art that determine the sequence of a nucleic acid strand.

In one embodiment of the invention, "x" can be selected from 1-10, 10-20, 20-30, 30-40, 40-50, 50-60, 60-70, 70-80, 80-90 or 90-100 nucleotides. In an another embodiment, "x" can be 100-200, 200-300, 300-400 or 400-500 nucleotides.

In another embodiment of the invention, if the probability of match of the sequence information of "n" length nucleotide fragment is less than a threshold of a target match, then "n+x" represents a minimal length of the nucleotide fragment for a positive identification of the nucleic acid molecule(s) obtained from said sample.

Another embodiment of the is a method of identifying a biological material in a sample, comprising: (i) obtaining a sample comprising said biological material, (ii) extracting one or more nucleic acid molecule(s) from said sample, (iii) generating sequence information, comprising a sequence of a nucleotide fragment from said one or more nucleic acid molecule(s), (iv) comparing said sequence of a nucleotide fragment to nucleic acid sequences in a database; and if said comparison of said sequence of a nucleotide fragment does not result in a match identifying the biological material in said sample, then the method further comprises: (v) generating additional sequence information from said one or more nucleic acid molecule(s), wherein said additional sequence information comprises a sequence of a nucleotide fragment consisting of one additional nucleotide, (vi) comparing said additional sequence information to nucleic acid sequences in a database immediately following the generation of said additional sequence information; and repeating steps (v)-(vi) until a match results in the identification of the biological material is said sample.

Another embodiment of the invention is a method of identifying a biological material in a sample, comprising: (i) obtaining a sample comprising said biological material, (ii) extracting one or more nucleic acid molecule(s) from said sample, (iii) amplifying said one or more nucleic acid molecule(s) to yield a plurality of one or more nucleic acid molecule(s), (iii) generating a plurality of sequence information, comprising a plurality of sequences of a nucleotide fragment, from said plurality of one or more nucleic acid molecule(s), (iv) comparing said plurality of sequences of a nucleotide fragment to nucleic acid sequences in a database, and if said comparison of said plurality of sequences of a nucleotide fragment does not result in a match identifying the biological material in said sample, then the method further comprises: (v) generating plurality of additional sequence information from said one or more nucleic acid molecule(s), wherein said additional sequence information comprises a sequence of a nucleotide fragment consisting of one additional nucleotide, (vi) comparing said additional sequence information to nucleic acid sequences in a database immediately following the generation of said additional sequence information, and repeating steps (v)-(vi) until a match results in the identification of the biological material is said sample.

The present invention is also directed to a system for detecting biological material, comprising: (i) a sample receiving unit configured to receive a sample comprising biological material; (ii) an extraction unit in communication with said sample receiving unit, said extraction unit being configured to extract at least one nucleic acid molecule from said sample; (iii) sequencing cassette in communication with said extraction unit, said sequencing cassette being configured to receive said at least one nucleic acid molecule from said extraction unit and generate sequence information from said at least one nucleic acid molecule; (iv) a database comprising reference nucleic acid sequences; and a (v) processing unit in communication with said sequencing cassette and said database, said processing unit being configured to receive said sequence information from said sequencing cassette and compare said sequence information to said reference nucleic acid sequences.

In another embodiment of the invention, said extraction unit is configured to compare said nucleotide fragment of "n" length to a database.

In another embodiment of the invention, said extraction unit is configured to compare said nucleotide fragment of "n" length to a database via probabilistic matching.

In another embodiment of the invention, said extraction unit is configured to compare said nucleotide fragment of "n" length to a database in real time, or as fast as said fragment is generated.

In another embodiment of the invention, if the probability of match of a nucleotide fragment of "n" length is less than a threshold of a target match, then said sequencing cassette is configured to generate sequence information comprising nucleotide fragments varying in length (for example, increased, decreased or same length as previously generated sequence information) from said one or more nucleic acid molecule(s), and said extraction unit is configured to compare said nucleotide fragments of varying length to the nucleic acid sequences in a database.

Yet another embodiment of the invention comprises a system, wherein said nucleotide fragment of "n" length is compared to said reference nucleic acid sequences in real time, or as fast as said fragment of "n" length is generated, while the sequencing unit continues to generate sequence information of "n+1", "n+2" ... "n+x" nucleotide fragments in length from said one or more nucleic acid molecule(s), and the processing unit compares said sequence information of "n+1", "n+2" ... "n+x" nucleotide fragments in length, in real-time, or as fast as the fragments are generated to the nucleic acid sequences in a database.

Further variations encompassed within the system are described in the detailed description of the invention below.

BRIEF DESCRIPTION OF THE DRAWINGS

Various embodiments are described with reference to the accompanying drawings. In the drawings, like reference numbers indicate identical or functionally similar components.

DETAILED DESCRIPTION OF THE INVENTION

The methods and system described in the current invention use(s) the shortest unique sequence information, which in a mixture of nucleic acids in an uncharacterized sample have the minimal unique length (n) with respect to the entire sequence information generated or collected. In addition to unique length sequences, non-unique are also compared. The probability of identification of a genome increases with multiple matches. Some genomes will have longer minimal unique sequences than other genomes. The matching method of short length (n) sequences continues in parallel with sequence information generation or collection. The comparisons occur as fast as (real-time) subsequent longer sequences are generated or collected. This results in considerable decision space reduction because the calculations are made early in terms of sequence information generation/collection. The probabilistic matching may include, but not limited to, perfect matching, subsequence uniqueness, pattern matching, multiple sub-sequence matching within n length, inexact matching, seed and extend, distance measurements and phylogentic tree mapping. It provides an automated pipeline to match the sequence information as fast as it is generated or in real-time. The sequencing instrument can continue to collect longer and more strings of sequence information in parallel with the comparison. Subsequent sequence information can also be compared and may increase the confidence of a genome or species identification in the sample. The method does not need to wait for sequence information assembly of the short reads into larger contigs.

The system and methods disclosed herein provide nucleic acid intake, isolation and separation, DNA sequencing, database networking, information processing, data storage, data display, and electronic communication to speed the delivery of relevant data to enable diagnosis or identification of organisms with applications for pathogenic outbreak and appropriate responses. The system includes a portable sequencing device that electronically transmits data to a database for identification of organisms related to the determination of the sequence of nucleic acids and other polymeric or chain type molecules and probabilistic data matching.

Figure 1:
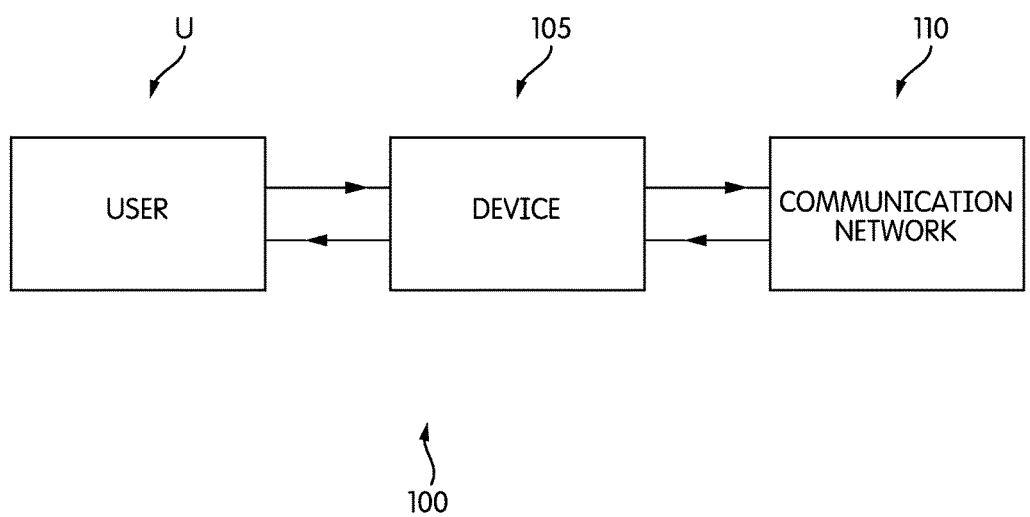
FIG. 1 is a schematic illustration of a disclosed system.
Figure 2:
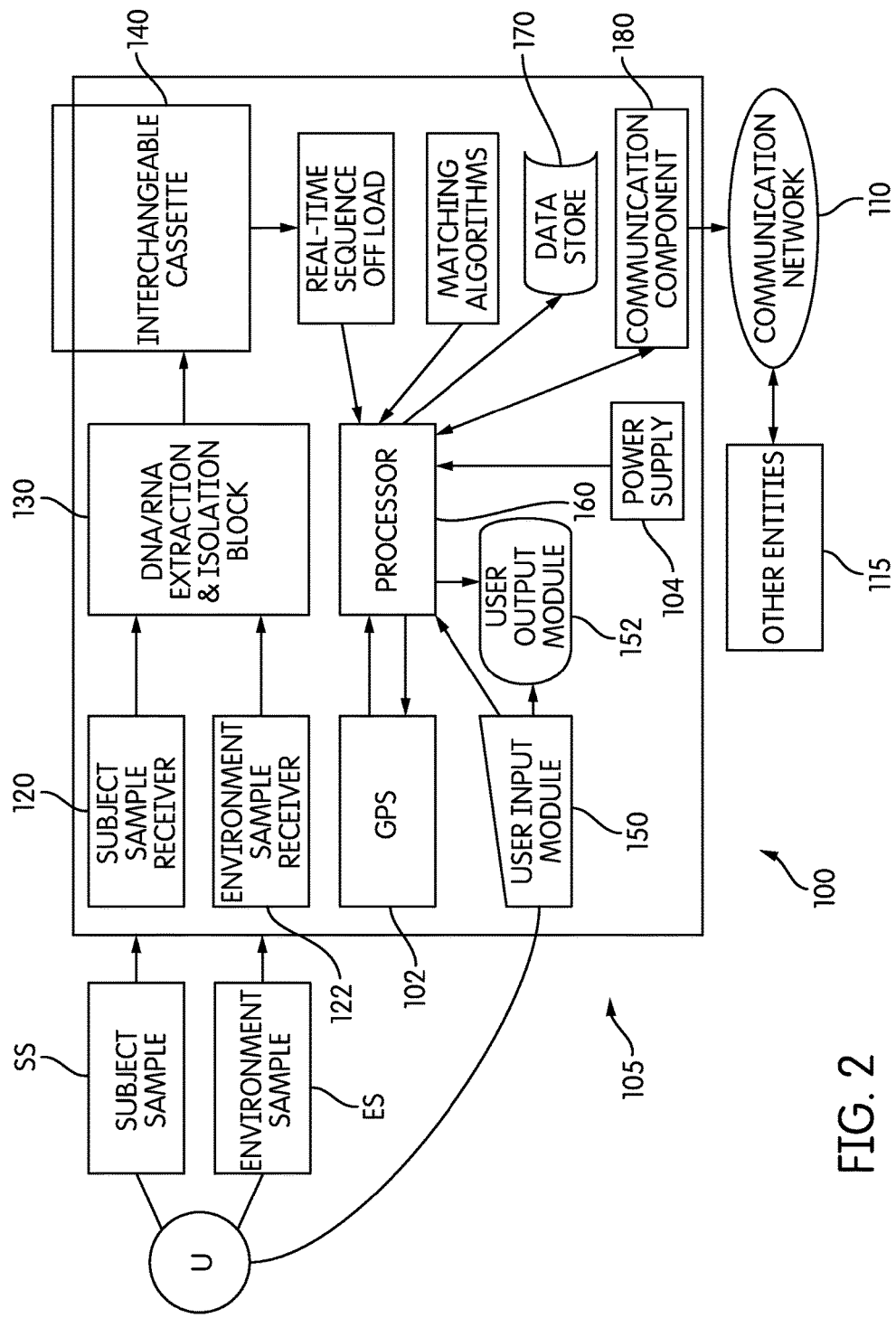
FIG. 2 is a more detailed schematic illustration of the system of FIG. 1.

FIGS. 1 and 2 illustrate an embodiment of a system 100 that includes a portable handheld electronic sequencing device 105. The portable electronic sequencing device 105 (referred to herein as "sequencing device") is configured to be readily held and used by a user (U), and can communicate via a communication network 110 with many other potentially relevant entities.

The device is configured to receive a subject sample (SS) and an environment sample (ES), respectively. The subject sample (such as blood, saliva, etc), can include the subject's DNA as well as DNA of any organisms (pathogenic or otherwise) in the subject. The environment sample (ES) can include, but not limited to, organisms in their natural state in the environment (including food, air, water, soil, tissue). Both samples (SS, ES) may be affected by an act of bioterrorism or by an emerging epidemic. Both samples (SS, ES) are simultaneously collected via a tube or swab and are received in a solution or solid (as a bead) on a membrane or slide, plate, capillary, or channel. The samples (SS, ES) are then sequenced simultaneously. Circumstance specific situations may require the analysis of a sample composed of a mixture of the samples (SS, ES). A first responder can be contacted once a probabilistic match is identified and/or during real-time data collection and data interpretation. As time progresses an increasing percentage of the sequence can be identified.

Figure 3:
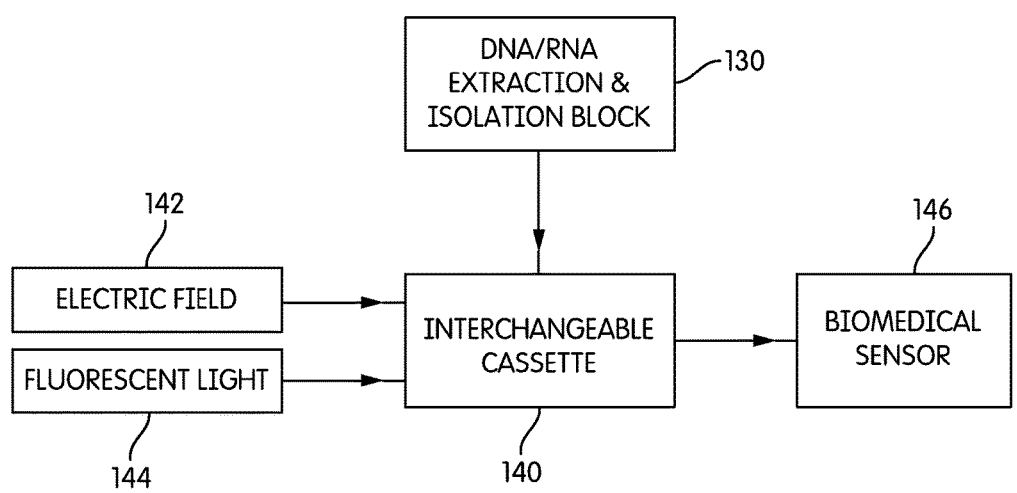
FIG. 3 is a schematic illustration of functional interaction between the interchangeable cassette and other components in an embodiment of the system of FIG. 1.

The sequencing device 105 can include the following functional components, as illustrated in FIG. 3, which enable the device 105 to analyze a subject sample (SS) and an environment sample (ES), communicate the resulting analysis to a communication network 110.

Sample receivers 120 and 122 are coupled to a DNA Extraction and Isolation Block 130, which then deliver the samples to Block 130 via a flow system. Block 130 extracts DNA from the samples and isolates it so that it may be further processed and analyzed. This can be accomplished by use of a reagent template (i.e. a strand of DNA that serves as a pattern for the synthesis of a complementary strand of nucleic acid), which may be delivered combined with the samples 120, 122 using known fluidic transport technology. The nucleic acids in the samples 120, 122 are separated by the Extraction and Isolation Block 130, yielding a stream of nucleotide fragments or unamplified single molecules. An embodiment could include the use of amplification methods.

An interchangeable cassette 140 may be removeably coupled to sequencing device 105 and block 130. The cassette 140 can receive the stream of molecules from block 130 and can sequence the DNA and produce DNA sequence data.

The interchangeable cassette 140 can be coupled to, and provide the DNA sequence data to the processor 160, where the probabilistic matching is accomplished. An embodiment could include performance of 16 GB of data transferred at a rate of 1 Mb/sec. A sequencing cassette 140 is preferred to obtain the sequence information. Different cassettes representing different sequencing methods may be interchanged. The sequence information is compared via probabilistic matching. Ultra-fast matching algorithms and pre-generated weighted signature databases compare the de novo sequence data to stored sequence data.

The processor 160 can be, for example, an application-specific integrated circuit designed to achieve one or more specific functions or enable one or more specific devices or applications. The processor 160 can control all of the other functional elements of sequencing device 105. For example, the processor 160 can send/receive the DNA sequence data to be stored in a data store (memory) 170. The data store 170 can also include any suitable types or forms of memory for storing data in a form retrievable by the processor 160.

The sequencing device 105 can further include a communication component 180 to which the processor 160 can send data retrieved from the data store 170. The communication component 180 can include any suitable technology for communicating with the communication network 110, such as wired, wireless, satellite, etc.

The sequencing device 105 can include a user input module 150, which the user (U) can provide input to the device 105. This can include, any suitable input technology such as buttons, touch pad, etc. Finally the sequencing device 105 can include a user output module 152 which can include a display for visual output and/or an audio output device.

The sequencing device 105 can also include a Global Positioning System (GPS) receiver 102, which can receive positioning data and proceed the data to the processor 160, and a power supply 104 (i.e. battery, plug-in-adapter) for supplying electrical or other types of energy to an output load or group of loads of the sequencing device 105.

The interchangeable cassette 140 is illustrated schematically in more detail in FIG. 3. The cassette 140 may be removeably coupled to sequencing device 105 and block 130 and includes a state of the art sequencing method (i.e. high throughput sequencing). Wet chemistry or solid state based system may be built on deck via a cassette exchangeable "plug & play" fashion. The cassette 140 can receive the stream of molecules from block 130 and can sequence the DNA via the sequencing method and can produce DNA sequence data. Embodiments include methods based on, but not limited to, Sequencing-by-synthesis, Sequencing-by-ligation, Single-molecule-sequencing and Pyrosequencing. A yet another embodiment of includes a source for electric field 142 and applies the electric field 142 to the stream of molecules to effect electrophoresis of the DNA within the stream. The cassette includes a light source 144 for emitting a fluorescent light 144 through the DNA stream. The cassette further includes a biomedical sensor (detector) 146 for detecting the fluorescent light emission and for detecting/determining the DNA sequence of the sample stream. In addition to fluorescent light, the biomedical sensor is capable of detecting light at all wavelengths appropriate for labeled moieties for sequencing.

The fluorescent detection comprises measurement of the signal of a labeled moiety of at least one of the one or more nucleotides or nucleotide analogs. Sequencing using fluorescent nucleotides typically involves photobleaching the fluorescent label after detecting an added nucleotide. Embodiments can include bead-based fluorescent, FRET, infrared labels, pyrophosphatase, ligase methods including labeled nucleotides or polymerase or use of cyclic reversible terminators. Embodiments can include direct methods of nanopores or optical waveguide including immobilized single molecules or in solution. Photobleaching methods include a reduced signal intensity, which builds with each addition of a fluorescently labeled nucleotide to the primer strand. By reducing the signal intensity, longer DNA templates are optionally sequenced.

Photobleaching includes applying a light pulse to the nucleic acid primer into which a fluorescent nucleotide has been incorporated. The light pulse typically comprises a wavelength equal to the wavelength of light absorbed by the fluorescent nucleotide of interest. The pulse is applied for about 50 seconds or less, about 20 seconds or less, about 10 seconds or less, about 5 seconds or less, about 2 seconds or less, about 1 seconds or less, or about 0. The pulse destroys the fluorescence of the fluorescently labeled nucleotides and/or the fluorescently labeled primer or nucleic acid, or it reduces it to an acceptable level, e.g., a background level, or a level low enough to prevent signal buildup over several cycles.

The sensor (detector) 146 optionally monitors at least one signal from the nucleic acid template. The sensor (detector) 146 optionally includes or is operationally linked to a computer including software for converting detector signal information into sequencing result information, e.g., concentration of a nucleotide, identity of a nucleotide, sequence of the template nucleotide, etc. In addition, sample signals are optionally calibrated, for example, by calibrating the microfluidic system by monitoring a signal from a known source.

As shown in FIG. 2, the sequencing device 105 can communicate via a communication network 110 with a variety of entities that may be relevant to notify in the event of a bioterrorist act or an epidemic outbreak. These entities can include a First Responder (i.e. Laboratory Response Network (i.e. Reference Labs, Seminal Labs, National Labs), GenBank®, Center for Disease Control (CDC), physicians, public health personnel, medical records, census data, law enforcement, food manufacturers, food distributors, and food retailers.

Figure 4:
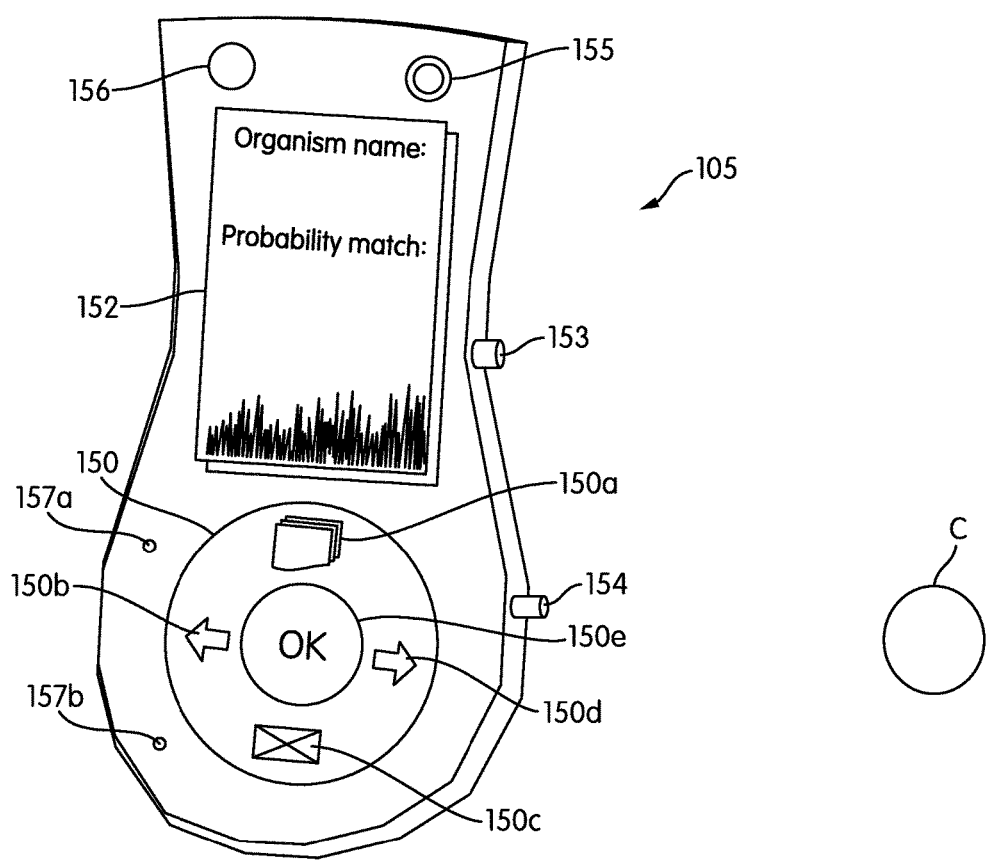
FIG. 4 is a front perspective view of an embodiment of a handheld electronic sequencing device.

One example embodiment of the sequencing device 105 discussed above is now described with reference to FIG. 4 illustrating an anterior view of the device. The device is a portable handheld sequencing device and is illustrated in comparison with, the size of coins C. The device 105 is approximately 11 inches in length and easily transportable. (In FIG. 4, coins are shown for scale.) Two ports 153, 154 are located on a side of the device and represent sample receivers 120, 122. Port 153 is for receiving a subject sample (SS) or an environment sample (ES) to be analyzed and sequenced. Port 154 is for sequencing control (SC). The two different ports are designed to determine if a subject sample (SS) or environment sample (ES) contains materials that result in sequencing failure, should sequencing failure occur, or function in a CLIA capacity. The device 105 includes a user input module 150, which the user (U) can provide input to the device 105. In this particular embodiment, the user input module 150 is in the form of a touch pad, however, any suitable technology can be used. The touch pad includes buttons 150a for visual display, 150b, 150c for recording data, 150d for real-time data transmission and receiving, and 150e for power control for activating or deactivating the device. Alternatively, the key pad can be incorporated into the display screen and all functions can be controlled by liquid crystal interface. Suitable techniques are described in US Patent Pub. No. application 2007/0263163, the entire disclosure of which is hereby incorporated by reference. This can be by Bluetooth-enabled device pairing or similar approaches. The functions include digit keys, labeled with letters of the alphabet, such as common place on telephone keypads, such as a delete key, space key, escape key, print key, enter key, up/down, left/right, additional characters and any others desired by the user. The device further includes a user output module 152, in the form of a visual display, for displaying information for the user (U). An audio output device can also be provided if desired as illustrated at 157a and 157b. Finally, the sequencing device 105 includes light emitting diodes 155 and 156 to indicate the transmission or receiving of data. The function of the keys/buttons are to control all aspects of sample sequencing, data transmission and probabilistic matching and interface controls, including but not limited to on/off, send, navigation key, soft keys, clear, and LCD display functions and visualization tools with genome rank calculated by algorithms to list the confidence of matches. An embodiment includes an internet based system where multiple users may simultaneously transmit/receive data to/from a hierarchical network search engine.

Figure 5:
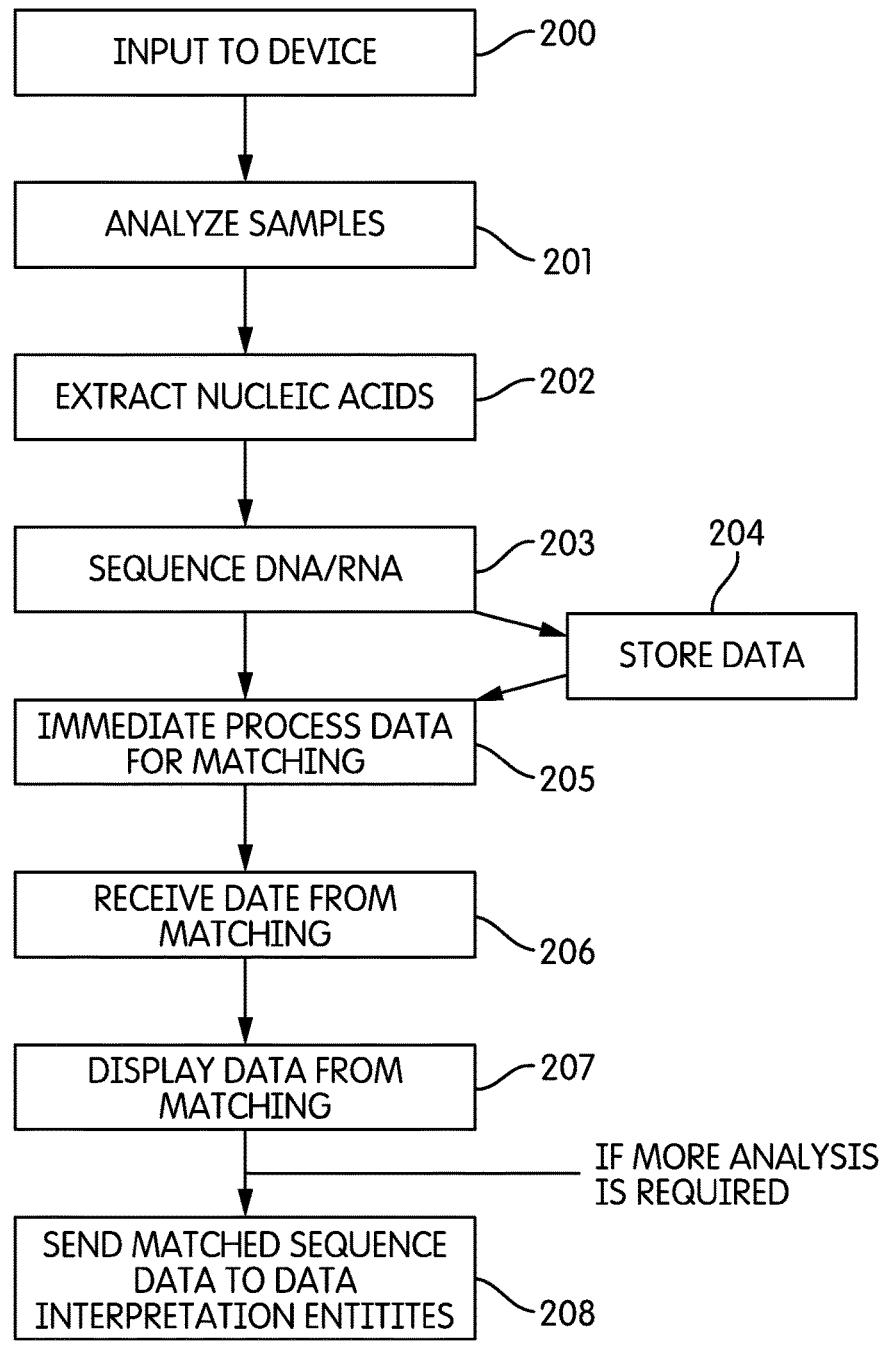
FIG. 5 is a flow chart illustrating a process of operation of the system of FIG. 1.

FIG. 5 is a flow chart illustrating a process of operation of the system 100 of an embodiment of the system 100 as described above. As shown in FIG. 5, a process of the device's operation includes at 200 receiving collected subject samples (SS) and environment sample (ES) in sample receivers 120, 122. At 202, the samples proceed to the DNA Extraction and Isolation Block 130 where the sample is analyzed and the DNA is extracted from the samples and isolated. At 203, the interchangeable cassette 140 receives the isolated DNA from block 130 and sequences the DNA. Depending on the cassette and if needed, with the application of an electric field 142 and of a fluorescent light 144, a biomedical sensor 146 within the cassette 140 detects/determines the DNA sequence of the sample stream. At 204, the sequenced data is processed and stored in a data store 170. At 205, the sequenced data is compared via probabilistic matching and genome identification is accomplished. The process is reiterative in nature. Resultant information may be transmitted via a communication network 110. GPS (global positioning system) data may optionally be transmitted as well at step 205. At 206, the device electronically receives data from matching. At 207, the device visually displays the data electronically received from matching via a user output module 152. If further analysis is require, at 208, the sequenced data is electronically transmitted to data interpretation entities (i.e. Public Health Personnel, Medical Records, etc.) via the communication network.

A multi-method research approach may enhance the rapid response to an incident and integrate primary care with organism detection. A triangulate response may be utilized, which involves quantitative instrument data from the DNA sequencing to converge with qualitative critical care. An infrastructure of observational checklists and audits of DNA sequencing data collected in the field across multiple locations may used to compare the appearance of an organism, e.g., bio-threat between locations. Inferential statistical analysis of the genomic data may combined with medical observations to develop categories of priorities. Information collected and shared between databases of medical centers and genomic centers may enable triangulation of an incident, the magnitude of the incident, and the delivery of the correct intervention to the affected people at the appropriate time.

Figure 6:
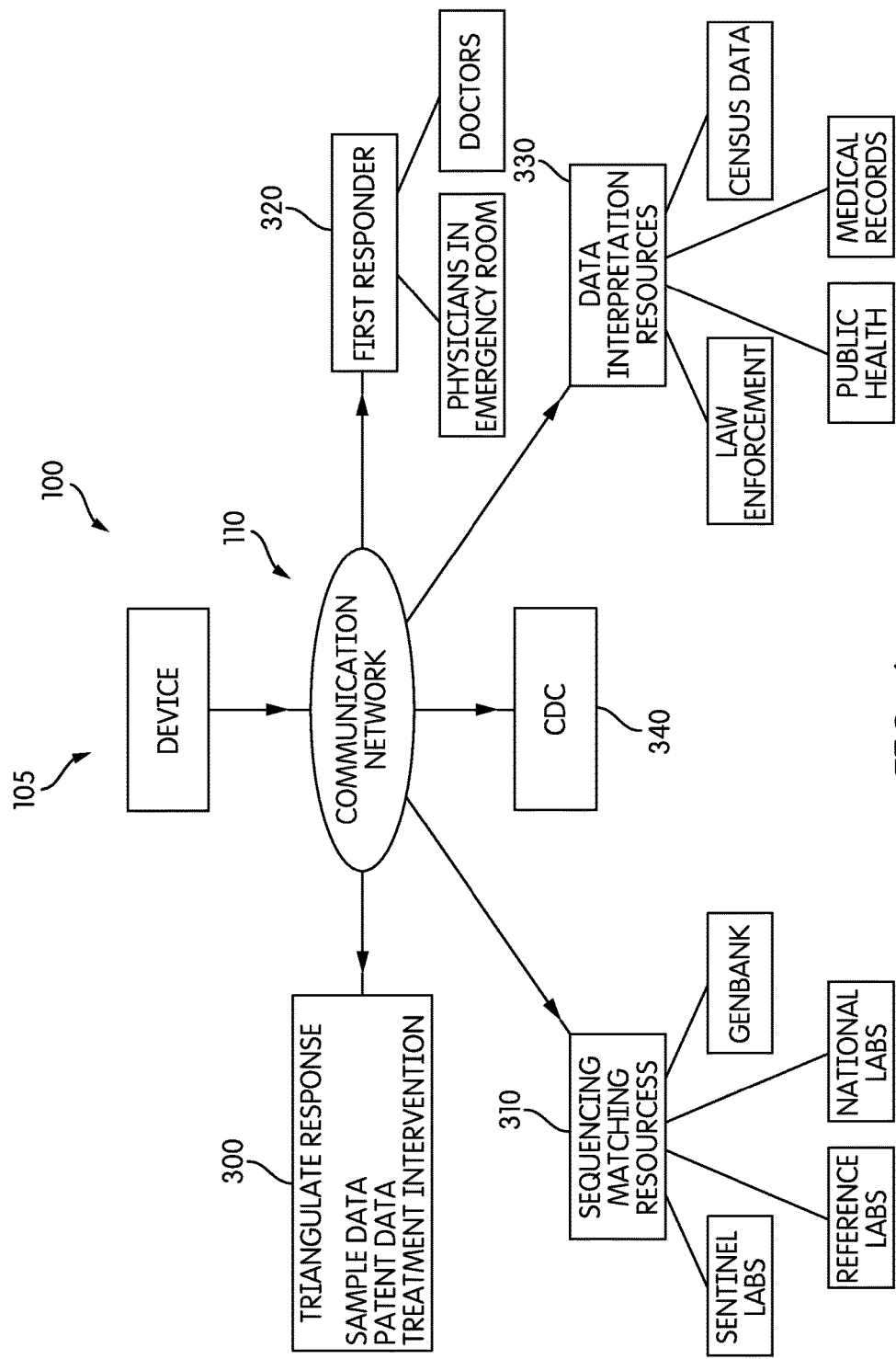
FIG. 6 is a schematic illustration of the interaction of the system of FIG. 1 with various entities potentially involved with the system.

FIG. 6 illustrates the interaction between the system 100 and various potential resources entities. The device 105 is configured to interact with these resource entities via a wireless or wired communication network. Device 105 can transmit triangulated sequenced data information (310) illustrating the "Sample Data", the "Patient Data", and "Treatment Intervention." Device 105 can transmit and receive DNA sequence data to and from sequence matching resources 320, which include GenBank® and a laboratory response network including Sentinel Labs, Reference Labs, and National Labs.

Each of the laboratories has specific roles. Sentinel laboratories (hospital and other community clinical labs) are responsible for ruling out or referring critical agents that they encounter to nearby LRN reference laboratories. Reference laboratories (state and local public health laboratories where Biological Safety Level 3 (BSL-3) practices are observed) perform confirmatory testing (rule in). National laboratories (BSL-4) maintain a capacity capable of handling viral agents such as Ebola and variola major and perform definitive characterization.

System 100 can further transmit and receive data to and from Data Interpretation Resources 330 including law enforcement entities, public health personnel, medical records, and census data. Finally, the device 105 can transmit and receive data to and from a first responder 320 which include doctors or physicians in an emergency room. The system 100 overall is configured to communicate with the Center for Disease Control (CDC) 340 to provide pertinent information to the proper personnel.

Figure 7:
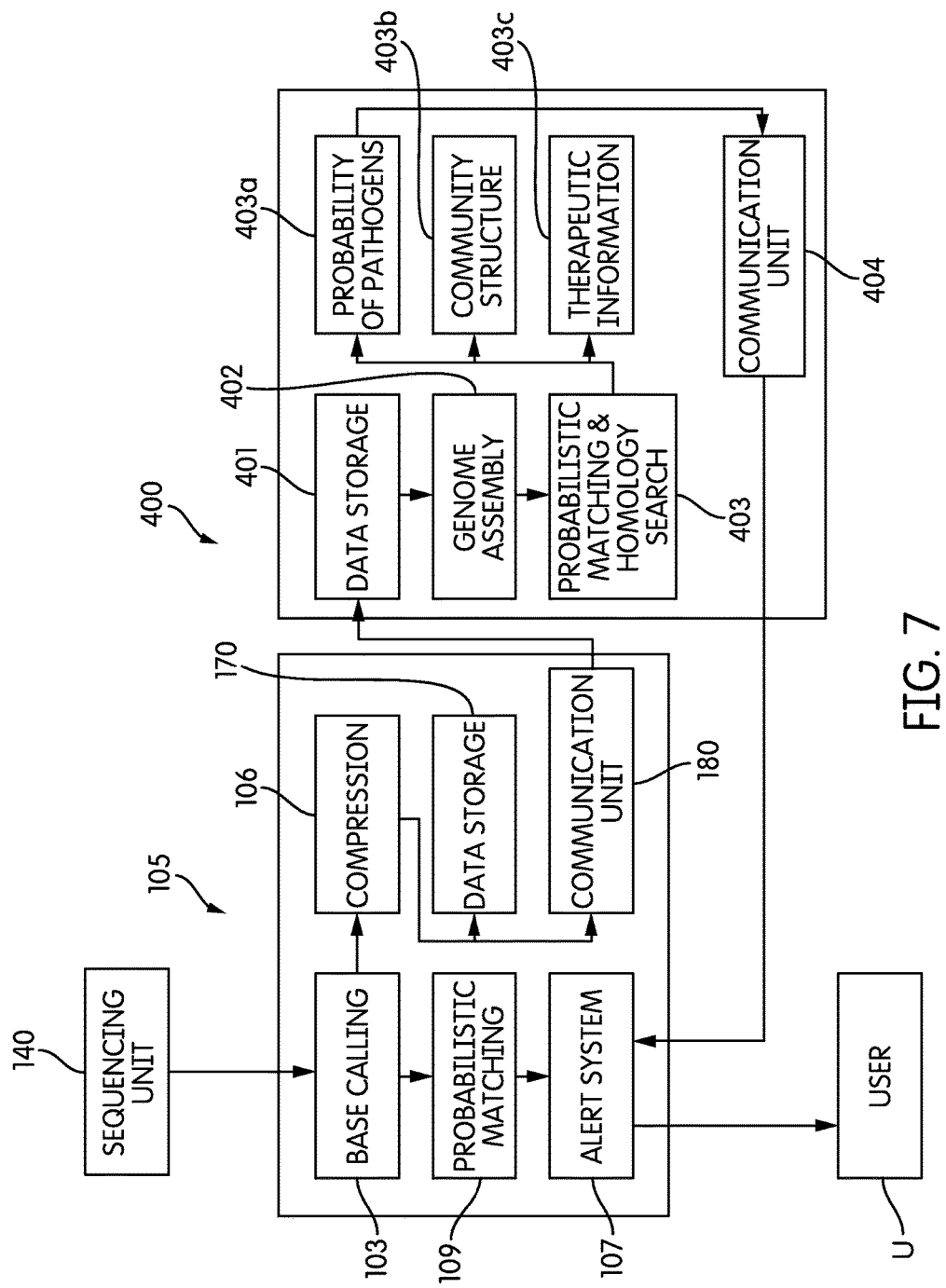
FIG. 7 is a schematic illustration of functional interaction between a hand held electronic sequencing device with the remote analysis center.

FIG. 7 is a schematic illustration of functional interaction between a hand held electronic sequencing device with the remote analysis center. The device 105 may include a base calling unit 103 for processing sequencing received by the interchangeable cassette 140. Such sequences and SNP sites are individually weighted according to its probability found in each species. These weights can be calculated either theoretically (by simulation) or experimentally. The device also includes a probabilistic matching processor 109 coupled to the base calling unit 103. The probabilistic matching is performed in real time or as fast as the sequence base calling or sequence data collection. The probabilistic matching processor 109, using a Bayesian approach, can receive resultant sequence and quality data, and can calculate the probabilities for each sequencing-read while considering sequencing quality scores generated by the base calling unit 103. The probabilistic matching processor 109 can use a database generated and optimized prior to its use for the identification of pathogens. An alert system 107 is coupled to the probabilistic matching processor 109 and can gather information from the probabilistic matching processor 109 (on site) and display the best matched organism(s) in real-time.

The alert system 107 is configured to access patient data, i.e. the medical diagnosis or risk assessment for a patient particularly data from point of care diagnostic tests or assays, including immunoassays, electrocardiograms, X-rays and other such tests, and provide an indication of a medical condition or risk or absence thereof. The alert system can include software and technologies for reading or evaluating the test data and for converting the data into diagnostic or risk assessment information. Depending on the genome identity of the bio-agent and the medical data about the patient, an effective "Treatment Intervention" can be administered. The treatment can be based on the effective mitigation or neutralization of the bio-agent and/or its secondary effects and based on the patient history if there are any contra-indications. The alert system can be based on the degree and number of occurrences. The number of occurrences can be based on the genomic identification of the bio-agent. A value can be pronounced when the result is within or exceeds a threshold as determined by government agencies, such as the CDC or DoD or Homeland Security. The alert system is configured to enable clinicians to use the functionality of genomic identification data with patient data. The communication permits rapid flow of information and accurate decision making for actions by first responders or other clinical systems.

The device 105 further includes a data compressor 106 coupled to the base calling unit 103, configured to receive the resultant sequence and quality data for compression. The data store 170 is coupled to the compressor 106 and can receive and store the sequence and quality data.

The sequencing device 105 interacts with a remote analysis center 400, which can receive electronically transferred data from the communication component 180 of the sequencing device 105 via a wired and/or wireless communication method. The remote analysis center 400 contains a large sequence database including all of nucleotide and amino acid sequences and SNP data available to date. This database also contains associated epidemiological and therapeutic information (e.g. antibiotic resistance). The remote analysis center 400 further includes a data store 401. The data store 401 can receive decompressed sequence data information via electronic transmission from the communication component 180 of the sequencing device 105. A genome assembly 402 is coupled to the data store 401 and can and assemble the decompressed sequence data. Obvious contaminant DNA, such as human DNA, can be filtered prior to further analysis.

The remote analysis center 400 further includes a processor 403 equipped with probabilistic matching technology and homology search algorithms, which can be employed to analyze assembled sequence data to obtain the probabilities of the presence of target pathogens 403a, community structure 403b, epidemiological and therapeutic information 403c. Genome sequence data of target pathogens are compared with those of genomes of non-pathogens including human and metagenome to identify nucleotide sequences and single nucleotide polymorphic (SNP) sites, which only occur in target organisms. The analysis at the remote analysis center 400 is carried out on the fly during data transfer from the sequencing device 105. The remote analysis center 400 can further include a communication unit 404 from which the analysis results are electronically transferred back to the alert system 107 within the sequencing device 105 as well as other authorities (e.g. DHS, CDC etc.).

Probabilistic Classification: The present invention provides database engines, database design, filtering techniques and the use of probability theory as Extended Logic. The instant methods and system utilizes the probability theory principles to make plausible reasoning (decisions) on data produced by nucleic acid sequencing. Using the probability theory approach, the system described herein analyzes data as soon as it reaches a minimal number of nucleotides in length (n), and calculating the probability of the n-mer, further each subsequent increase in length (n+base pair(s)) is used to calculate the probability of a sequence match. The calculation of each n-mer and subsequent longer n-mers is further processed to recalculate the probabilities of all increasing lengths to identify the presence of genome(s). As the unit length increases, multiple sub-units, within the n-mer are compared for pattern recognition, which further increases the probability of a match. Such method, including other Bayesian methods, provides for eliminating matches and identifying a significant number of biological samples comprising with a very short nucleotide fragment or read without having to complete full genome sequencing or assembling the genome. As such assigning the likelihood of the match to existing organisms and move on to the next nucleic acid sequence read to further improve the likelihood of the match. The system described herein increases speed, reduces reagent consumption, enables miniaturization, and significantly reduces the amount of time required to identify the organism.

In order to build probabilistic classifiers to make a decision on short nucleic acid sequences, a variety of approaches to first filter and later classify the incoming sequencing data can be utilized. In the instant case, the formalism of Bayesian networks is utilized. A Bayesian network is a directed, acyclic graph that compactly represents a probability distribution. In such a graph, each random variable is denoted by a node (for example, in a phylogenetic tree of an organism). A directed edge between two nodes indicates a probabilistic dependency from the variable denoted by the parent node to that of the child. Consequently, the structure of the network denotes the assumption that each node in the network is conditionally independent of its non-descendants given its parents. To describe a probability distribution satisfying these assumptions, each node in the network is associated with a conditional probability table, which specifies the distribution over any given possible assignment of values to its parents. In this case a Bayesian classifier is a Bayesian network applied to a classification task of calculating the probability of each nucleotide provided by any sequencing system. At each decision point the Bayesian classifier can be combined with a version of shortest path graph algorithm such, as Dijkstra's or Floyd's.

The current system may implement a system of Bayesian classifiers (for example, Naïve Bayesian classifier, Bayesian classifier and Recursive Bayesian estimation classifier) and fuse the resulting data in the decisions database. After the data is fused, each classifier may be fed a new set of results with updated probabilities.

Figure 8:
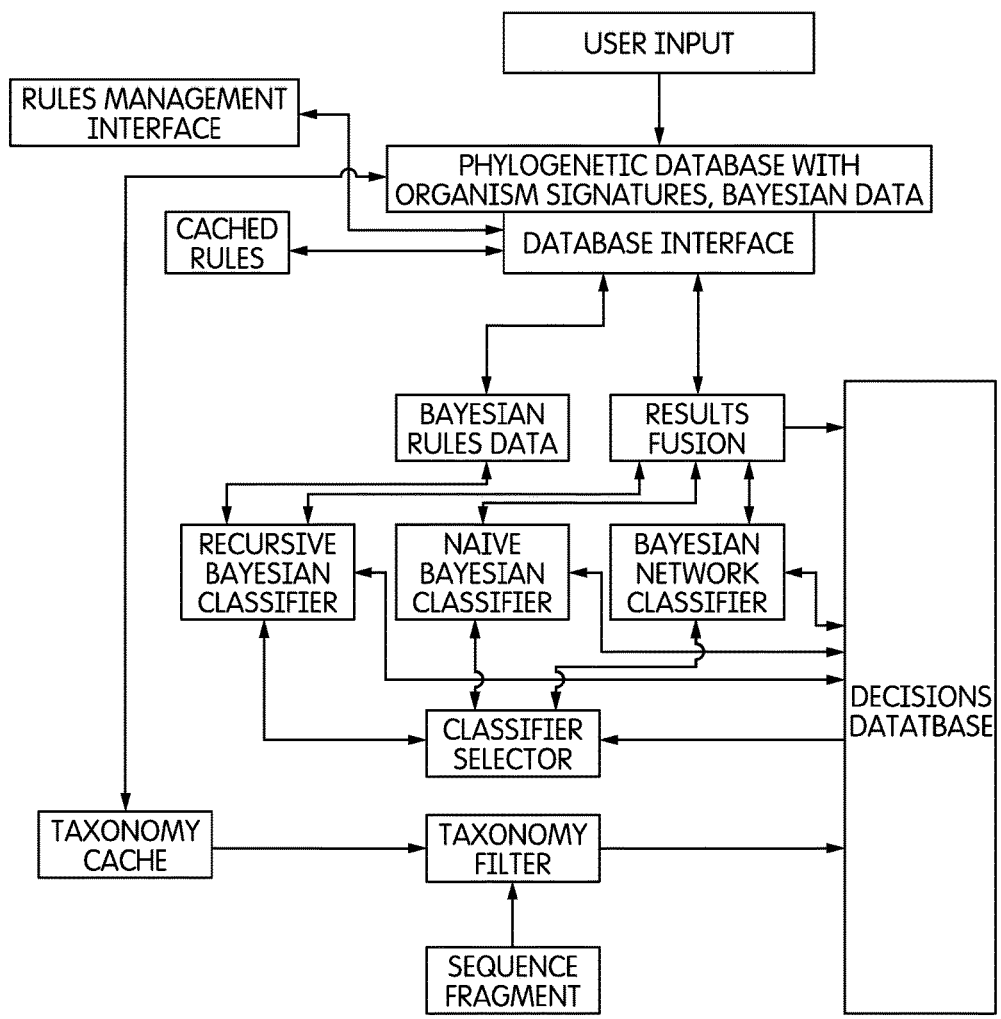
FIG. 8 is a schematic illustration of the overall architecture of the probabilistic software module.
Figure 9:
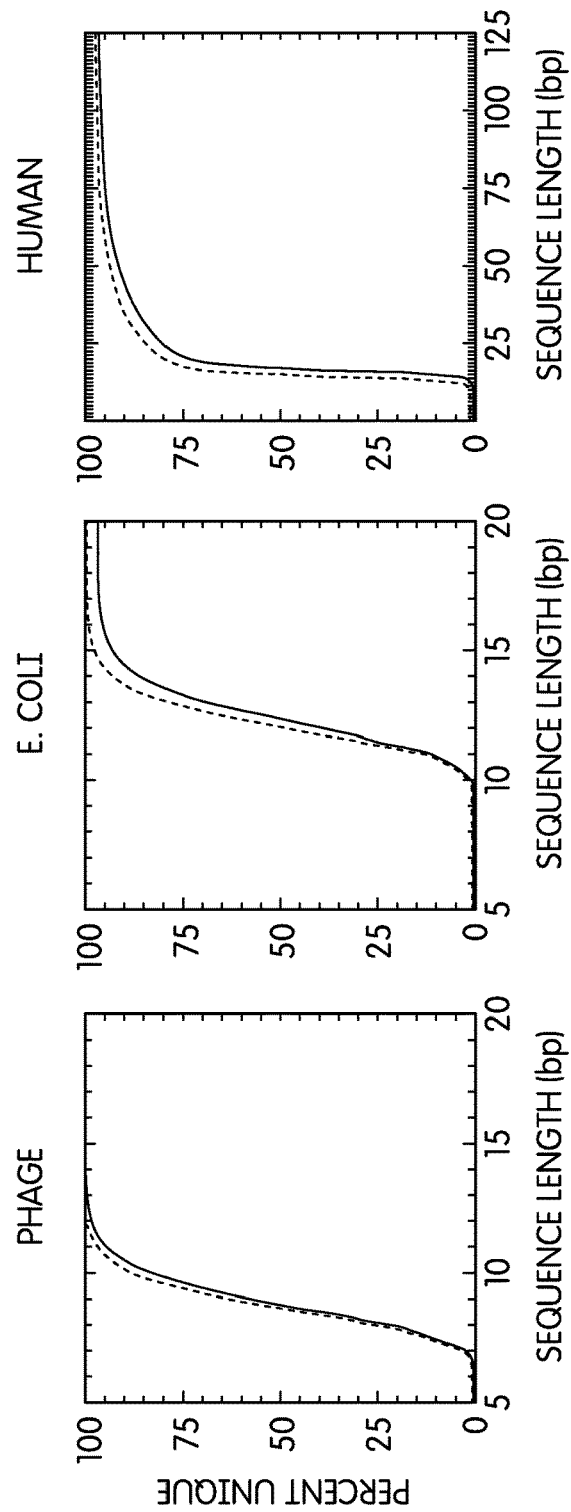
FIG. 9 shows the percentage of unique sequences as a function of read length.
Figure 10:
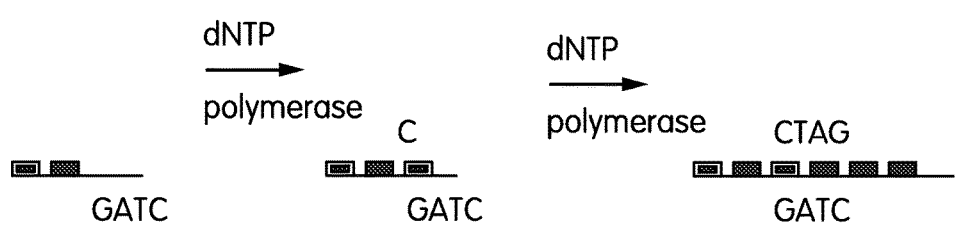
FIG. 10 is a summary of principle steps of sequencing.

FIG. 8 shows a schematic illustration of the overall architecture of the probabilistic software module.

DNA Sequencing Fragment: Any sequencing methods can be used to generate the sequence fragment information. The module, 160 in FIG. 2 or 109 in FIG. 7 is responsible for processing data incoming from Sequencing module in the interchangeable cassette. The data is encapsulated with sequencing data as well as information above start and stop of the sequence, sequence ID, DNA chain ID. The module formats the data and passes it to the taxonomy filter module. The formatting includes addition of the system data and alignment in chunks.

DNA Sequencing module has 2 interfaces. It is connected to DNA Prep module and to taxonomy Filter.

I. DNA Prep Interface: Several commercially available methods to accomplish sample preparation can be integrated via microfluidics techniques. Typical sample preparation is solution based and includes cell lysis and inhibitor removal. The nucleic acids are recovered or extracted and concentrated. Embodiments of the lysis include detergent/enzymes, mechanical, microwave, pressure, and/or ultrasonic methods. Embodiments of extraction include solid phase affinity and/or size exclusion.

II. Taxonomy Filter: Taxonomy filter has two main tasks: (i) Filter out as many organisms as possible to limit the classifier module to a smaller decision space, and (ii) Help determine the structure of the Bayesian network, which involves the use of machine learning techniques.

Phylogenetic tree filter: This sub-module of taxonomy filter interfaces with "Decisions Database" to learn the results of the previous round of analysis. If no results are found the module passes the new data to classification module. If the results are found the taxonomy filter adjusts classifier data to limit the possible decision space. For example if the prior data indicates that this is a virus DNA sequence that is being looked at, the decision space for the classifier will be shrunk to viral data only. This can be done by modifying the data Bayesian classifiers collected while operating.

Machine Learning: Machine learning algorithms are organized into a taxonomy, based on the desired outcome of the algorithm. (i) Supervised learning—in which the algorithm generates a function that maps inputs to desired outputs. One standard formulation of the supervised learning task is the classification problem: the learner is required to learn (to approximate) the behavior of a function which maps a vector $[X_1, X_2, \ldots X_N]$ into one of several classes by looking at several input-output examples of the function. (ii) Semi-supervised learning—which combines both labeled and unlabeled examples to generate an appropriate function or classifier. (iii) Reinforcement learning—in which the algorithm learns a policy of how to act given an observation of the world. Every action has some impact in the environment, and the environment provides feedback that guides the learning algorithm. (iv) Transduction—predicts new outputs based on training inputs, training outputs, and test inputs which are available while training. (v) Learning to learn—in which the algorithm learns its own inductive bias based on previous experience.

Taxonomy Cache Module: The module caches taxonomy information produced by taxonomy filter. It can act as an interface between taxonomy filter and taxonomy database which holds all of the information in SQL database. Taxonomy cache is implemented as in-memory database with micro-second response timing. Queries to the SQL database are handled in a separate thread from the rest of the sub-module. Cache information includes the network graph created by the taxonomy filter module. The graph contains the whole taxonomy as the system starts analysis. DNA sequence analysis reduces the taxonomy graph with taxonomy cache implementing the reductions in data size and the removal of the appropriate data sets.

Classifier Selector: The instant system can utilize multiple classification techniques executing in parallel. Classifier selector can act as data arbiter between different classification algorithms. Classifier selector can reads information from the Decisions Database and push such information to the classification modules with every DNA sequencing unit received for analysis from DNA Sequencing Module. Taxonomy filter acts as data pass through for the DNA sequencing data.

Recursive Bayesian Classifier: Recursive Bayesian classifier is a probabilistic approach for estimating, an unknown probability density function recursively over time using incoming measurements and a mathematical process model. The module receives data from classifier selector and from the Decisions Database where prior decisions are stored. The data set is retrieved from the databases and prior decision identification placed in local memory of the module where the filtering occurs. The classifier takes DNA sequence and tries to match it with or without existing signatures, barcodes, etc., from the taxonomy database by quickly filtering out families of organisms that do not match. The algorithm works by calculating the probabilities of multiple beliefs and adjusting beliefs based on the incoming data. Algorithms used in this module may include Sequential Monte Carlo methods and sampling importance resampling. Hidden Markov Model, Ensemble Kalman filter and other particle filters may also be used together with Bayesian update technique.

Naïve Bayesian Classifier: Simple probabilistic classifier based on the application of the Bayes' theorem. The classifier makes all decisions based on the predetermined rule-set which is provided as user input at start-up. The module can be re-initialized with a new rule set while it is executing analysis. New rules set can come from the user or it can be a product of the rules fusion of The Results Fusions module.

Bayesian Network Classifier: Bayesian Network Classifier implements a Bayesian network (or a belief network) as a probabilistic graphical model that represents a set of variables and their probabilistic independencies.

Decisions Database: Decisions Database is a working cache for most modules in the system. Most modules have direct access to this resource and can modify their individual regions. However only Results Fusion module can access all data and modify the Bayesian rule sets accordingly.

Bayesian Rules Data: The module collects all Bayesian rules in binary, pre-compiled form. The rules are read-write to all Bayesian classifiers as well as Taxonomy Filter and Results Fusions modules. The rules are dynamically recompiled as changes are made.

Results Fusion: The module fuses the date from multiple Bayesian classifiers as well as other statistical classifiers that are used, Results Fusion module looks at the mean variance between generated answers for each classifier and fuses the data if needed.

Database Interface: Interface to the SQL database. The interface is implemented programmatically with read and write functions separated in different threads. MySQL is the database of choice however sqLite may be used for faster database speed.

Taxonomy Database: The database will hold multiple internal databases: taxonomy tree, indexed pre-processed tree, user input and rules.

Cached Rules: In-Memory cache of post-processed rules provided by the user.

Rules Management: Graphical management interface to the module

User Input: User created inference rules. The rules are used by Bayesian classifiers to make decisions.

The systems and methods of the invention are described herein as being embodied in computer programs having code to perform a variety of different functions. Particular best-of-class technologies (present or emerging) can be licensed components. Existing methods for the extraction of DNA include the use of phenol/chloroform, salting out, the use of chaotropic salts and silica resins, the use of affinity resins, ion exchange chromatography and the use of magnetic beads. Methods are described in U.S. Pat. Nos. 5,057,426, 4,923,978, EP Patents 0512767 A1 and EP 0515484B and WO 95/13368, WO 97/10331 and WO 96/18731, the entire disclosures of which are hereby incorporated by reference. It should be understood, however, that the systems and methods are not limited to an electronic medium, and various functions can be alternatively practiced in a manual setting. The data associated with the process can be electronically transmitted via a network connection using the Internet. The systems and techniques described above can be useful in many other contexts, including those described below.

Disease association studies: Many common diseases and conditions involve complex genetic factors interacting to produce the visible features of that disease, also called a phenotype. Multiple genes and regulatory regions are often associated with a particular disease or symptom. By sequencing the genomes or selected genes of many individuals with a given condition, it may be possible to identify the causative mutations underlying the disease. This research may lead to breakthroughs in disease detection, prevention and treatment.

Cancer research: Cancer genetics involves understanding the effects of inherited and acquired mutations and other genetic alterations. The challenge of diagnosing and treating cancer is further compounded by individual patient variability and hard-to-predict responses to drug therapy. The availability of low-cost genome sequencing to characterize acquired changes of the genome that contribute to cancer based on small samples or tumor cell biopsies, may enable improved diagnosis and treatment of cancer.

Pharmaceutical research and development: One promise of genomics has been to accelerate the discovery and development of more effective new drugs. The impact of genomics in this area has emerged slowly because of the complexity of biological pathways, disease mechanisms and multiple drug targets. Single molecule sequencing could enable high-throughput screening in a cost-effective manner using large scale gene expression analysis to better identify promising drug leads. In clinical development, the disclosed technology could potentially be used to generate individual gene profiles that can provide valuable information on likely response to therapy, toxicology or risk of adverse events, and possibly to facilitate patient screening and individualization of therapy.

Infectious disease: All viruses, bacteria and fungi contain DNA or RNA. The detection and sequencing of DNA or RNA from pathogens at the single molecule level could provide medically and environmentally useful information for the diagnosis, treatment and monitoring of infections and to predict potential drug resistance.

Autoimmune conditions: Several autoimmune conditions, ranging from multiple sclerosis and lupus to transplant rejection risk, are believed to have a genetic component. Monitoring the genetic changes associated with these diseases may enable better patient management.

Clinical diagnostics: Patients who present the same disease symptoms often have different prognoses and responses to drugs based on their underlying genetic differences. Delivering patient-specific genetic information encompass molecular diagnostics including gene- or expression-based diagnostic kits and services, companion diagnostic products for selecting and monitoring particular therapies, as well as patient screening for early disease detection and disease monitoring. Creating more effective and targeted molecular diagnostics and screening tests requires a better understanding of genes, regulatory factors and other disease- or drug-related factors, which the disclosed single molecule sequencing technology has the potential to enable.

Agriculture: Agricultural research has increasingly turned to genomics for the discovery, development and design of genetically superior animals and crops. The agribusiness industry has been a large consumer of genetic technologies—particularly microarrays—to identify relevant genetic variations across varieties or populations. The disclosed sequencing technology may provide a more powerful, direct and cost-effective approach to gene expression analysis and population studies for this industry.

Further opportunity will be in the arena of repeat-sequence applications where the methods are applied to the detection of subtle genetic variation. Expanded comparative genomic analysis across species may yield great insights into the structure and function of the human genome and, consequently, the genetics of human health and disease. Studies of human genetic variation and its relationship to health and disease are expanding. Most of these studies use technologies that are based upon known, relatively common patterns of variation. These powerful methods will provide important new information, but they are less informative than determining the full, contiguous sequence of individual human genomes. For example, current genotyping methods are likely to miss rare differences between people at any particular genomic location and have limited ability to determine long-range rearrangements. Characterization of somatic changes of the genome that contribute to cancer currently employ combinations of technologies to obtain sequence data (on a very few genes) plus limited information on copy number changes, rearrangements, or loss of heterozygosity. Such studies suffer from poor resolution and/or incomplete coverage of the genome. The cellular heterogeneity of tumor samples presents additional challenges. Low cost complete genome sequencing from exceedingly small samples, perhaps even single cells, would alter the battle against cancer in all aspects, from the research lab to the clinic. The recently-launched Cancer Genome Atlas (TCGA) pilot project moves in the desired direction, but remains dramatically limited by sequencing costs. Additional genome sequences of agriculturally important animals and plants are needed to study individual variation, different domesticated breeds and several wild variants of each species. Sequence analysis of microbial communities, many members of which cannot be cultured, will provide a rich source of medically and environmentally useful information. And accurate, rapid sequencing may be the best approach to microbial monitoring of food and the environment, including rapid detection and mitigation of bioterrorism threats.

Genome Sequencing could also provide isolated nucleic acids comprising intronic regions useful in the selection of Key Signature sequences. Currently, Key Signature sequences are targeted to exonic regions.

A fundamental application of DNA technology involves various labeling strategies for labeling a DNA that is produced by a DNA polymerase. This is useful in microarray technology: DNA sequencing, SNP detection, cloning, PCR analysis, and many other applications.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

Example 1

Purpose:
The use of key signatures and/or bar codes to enable genome identification with as few as 8-18 nucleotides and analysis of very short sequence data (reads) in real-time.

Linear time suffix array construction algorithms were used to calculate the uniqueness analysis. The analysis determined the percentage of all sequences that were unique in several model genomes. All sequence lengths in a genome were analyzed. Sequences that occur only once in a genome are counted. The suffix array algorithm works by calculating a repeat score plot which analyzes the frequency of specific subsequences within a sequence to occur based on a two base pair sliding window. Genome information stored in GenBank was used for the in-silico analysis. A viral genome, Lambda-phage, a bacterial genome, *E. coli* K12 MG1655, and the human genome were analyzed. The percentage of unique reads is a function of sequence length. An assumption was made concerning the sequences that only produce unambiguous matches and which produce unambiguous overlaps to reconstruct the genome. Unique reads ranged in size from 7 to 100 nucleotides. The majority of unique sizes were shorter than 9, 13, and 18 nucleotides, respectively.

Results: The results show that random sequences of 12 nt of the phage genome are 98% unique to phage. This increases slowly such that 400 nt sequences are 99% unique to phage. This decreases to 80% for phage sequences of 10 nt. For bacteria (*E. coli*) sequences of 18 nt of the genome are 97% unique to *E. coli*. For Human genomes, sequences of 25 nt are 80% unique to human and an increase to 45 nt results in 90% of the genome as unique.

What is claimed is:

1. A system for real-time identification of biological material in a sample potentially containing a plurality of nucleic acid molecules each from a corresponding one of a plurality of organisms, the sample being sequenced and analyzed in real-time, the system comprising:

a computer system comprising one or more processors programmed with computer program instructions that, when executed, cause the computer system to:

cause at least first nucleotide sequence information to be generated, the first nucleotide sequence information comprising a first string of one or more nucleotides generated from a first one of the plurality of nucleic acid molecules at a first time during real-time sequencing;

compare the first string of one or more nucleotides and one or more reference nucleic acid sequences stored in a reference database;

determine a probabilistic match between the first string of one or more nucleotides and the one or more reference nucleic acid sequences;

determine that the probabilistic match does not satisfy a predetermined threshold;

responsive to the determination that the probabilistic match does not satisfy the predetermined threshold, cause at least second nucleotide sequence information to be generated, the second nucleotide sequence information comprising a second string of one or more nucleotides generated from the first one of the plurality of nucleic acid molecules at a second time after the first time during real-time sequencing, wherein the second string of nucleotides includes at least one additional nucleotide generated from the first one of the plurality of nucleic acid molecules after the first time;

compare the second string of one or more nucleotides and the one or more reference nucleic acid sequences stored in the reference database;

determine a second probabilistic match between the second string of one or more nucleotides and at least one of the one or more reference nucleic acid sequences;

determine that the second probabilistic match satisfies the predetermined threshold;

determine a likelihood that one or more organisms corresponding to the at least one of the one or more reference nucleic acid sequences are present in the sample based at least in part on the second probabilistic match.

2. The system of claim 1, wherein the identities of the one or more organisms present in the biological material are determined at least to a sub-species level according to the likelihood determined based on the second probabilistic match.

3. The system of claim 1, further comprising a sequencer that generates the first nucleotide sequence information by sequencing the first one of the plurality of nucleic acid molecules.

4. The system of claim 3, wherein the second string of one or more nucleotides and a third string of one or more nucleotides are generated simultaneously at the sequencer.

5. The system of claim 1, further comprising an extractor configured to extract the first one of the plurality of nucleic acid molecules from the sample.

6. The system of claim 1, wherein a length of the second string of one or more nucleotides is less than 50.

7. The system of claim 1, wherein a length of the second string of one or more nucleotides is less than 20.

8. The system of claim 1, wherein the computer system is a handheld device.

9. The system of claim 1, wherein a subset of the one or more reference nucleic acid sequences in the reference database that do not match the first string of one or more nucleotides are removed from further analysis by a filtering process.

10. The system of claim 1, further comprising:

a sample receiving unit configured to receive the sample;
an extraction unit configured to extract the plurality of nucleic acid molecules from the sample; and a sequencing unit that receives the plurality of nucleic acid molecules from the extraction unit and generates at least the first nucleotide sequence information.

11. The system of claim 10, further comprising a storage unit in communication with the one or more processors, wherein the computer program instructions, when executed, cause the system to transmit data to the storage unit and subsequently retrieve the data from the storage unit for processing.

12. The system of claim 10, wherein the second string of one or more nucleotides and a third string of one or more nucleotides are generated simultaneously at the sequencing unit.

13. The system of claim 10, wherein the system is a handheld device.

14. The system of claim 1, wherein the computer system is further caused to:
   terminate sequencing of the first one of the plurality of nucleic acid molecules responsive to the determination that the second probabilistic match satisfies the predetermined threshold.

\* \* \* \* \*